United States Patent
Ogawa et al.

(10) Patent No.: US 10,172,964 B2
(45) Date of Patent: Jan. 8, 2019

(54) COMPOUND OR SALT THEREOF AND CONTRAST AGENT FOR OPTICAL IMAGING

(71) Applicant: CANON KABUSHIKI KAISHA, Tokyo (JP)

(72) Inventors: Satoshi Ogawa, Yokohama (JP); Masato Minami, Kawasaki (JP); Tatsuki Fukui, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 5 days.

(21) Appl. No.: 15/412,500

(22) Filed: Jan. 23, 2017

(65) Prior Publication Data

US 2017/0224850 A1    Aug. 10, 2017

(30) Foreign Application Priority Data

Feb. 8, 2016   (JP) ................................ 2016-021967

(51) Int. Cl.

| | | |
|---|---|---|
| *A61K 49/00* | (2006.01) | |
| *A61K 49/22* | (2006.01) | |
| *C09B 23/08* | (2006.01) | |
| *C09B 23/16* | (2006.01) | |
| *G01N 33/58* | (2006.01) | |
| *C08G 65/333* | (2006.01) | |
| *C08G 65/334* | (2006.01) | |

(52) U.S. Cl.
CPC ........ *A61K 49/221* (2013.01); *A61K 49/0032* (2013.01); *A61K 49/0054* (2013.01); *C08G 65/3348* (2013.01); *C08G 65/33337* (2013.01); *C09B 23/086* (2013.01); *C09B 23/164* (2013.01); *G01N 33/58* (2013.01)

(58) Field of Classification Search
CPC combination set(s) only.
See application file for complete search history.

(56) References Cited

U.S. PATENT DOCUMENTS

| | | |
|---|---|---|
| 8,753,608 B2 | 6/2014 | Tabata et al. |
| 9,132,203 B2 | 9/2015 | Tabata et al. |
| 9,138,492 B2 | 9/2015 | Fukui et al. |
| 9,416,276 B2 | 8/2016 | Fukui et al. |
| 9,517,278 B2 | 12/2016 | Takahashi et al. |
| 2011/0054181 A1 | 3/2011 | Koori et al. |
| 2012/0052011 A1 | 3/2012 | Fukui et al. |
| 2012/0052017 A1 | 3/2012 | Kato et al. |
| 2015/0126749 A1 | 5/2015 | Fukui et al. |
| 2015/0157741 A1 | 6/2015 | Yamauchi et al. |
| 2015/0290345 A1 | 10/2015 | Takahashi et al. |
| 2016/0067359 A1 | 3/2016 | Fukui et al. |
| 2016/0279271 A1 | 9/2016 | Yamauchi et al. |

FOREIGN PATENT DOCUMENTS

| | | |
|---|---|---|
| JP | 2011-46663 A | 3/2011 |
| WO | 2014/013732 A1 | 1/2014 |

OTHER PUBLICATIONS

Chemical Abstract Service, STN Registry Database [online], Registry No. 1062552-05-9 and 1062320-86-8 [Entered STN: Oct. 2008]. (Year: 2018).*
Chemical Abstract Service, STN Registry Database [online], Registry No. 705920-78-1 [Entered STN: Jul. 7, 2004]. (Year: 2004).*

* cited by examiner

*Primary Examiner* — Amanda L Aguirre
(74) *Attorney, Agent, or Firm* — Venable LLP

(57) ABSTRACT

A compound having a high tumor accumulation rate, or a salt thereof, and a contrast agent for optical imaging are provided. A compound having at least one specific organic dye covalently bound to polyethylene glycol, or a salt thereof is provided.

11 Claims, No Drawings

COMPOUND OR SALT THEREOF AND CONTRAST AGENT FOR OPTICAL IMAGING

BACKGROUND OF THE INVENTION

Field of the Invention

The present invention relates to a compound or a salt thereof, and a contrast agent for optical imaging.

Description of the Related Art

An optical imaging method is known as a method for visualizing information on the inside of a living body in a non-invasive manner. In the optical imaging method, a signal, such as an acoustic wave and fluorescence, emitted from a substance (light absorber) that absorbs light in a specimen in irradiation of the specimen with light is measured for imaging. A technique where a subject is irradiated with light and the fluorescence is measured for imaging is referred to as a fluorescence imaging method. A technique where a subject is irradiated with light and the acoustic wave is measured for imaging is referred to as photoacoustic imaging (hereinafter, sometimes abbreviated as "PAI").

An organic dye (hereinafter, near-infrared organic dye, alternatively, sometimes simply referred to as "dye") that absorbs light in a near-infrared wavelength region, such as indocyanine green (hereinafter, sometimes abbreviated as "ICG"), can also be administered to a living body to thereby allow the fluorescence and/or acoustic wave emitted from the organic dye in the living body to be measured. Accordingly, the organic dye such as ICG can be utilized as a contrast agent for optical imaging.

Japanese Patent Application Laid-Open No. 2011-46663 discloses a near-infrared organic dye as a contrast agent for optical imaging, and reports the following: various functional groups are introduced to a methine chain portion of the near-infrared organic dye to result in an improvement in tumor accumulation rate of the near-infrared organic dye.

SUMMARY OF THE INVENTION

In order that an image where a tumor site is more clearly seen is obtained in optical imaging, a larger amount of a contrast agent is required to be accumulated in a tumor. The near-infrared dye disclosed in Japanese Patent Application Laid-Open No. 2011-46663 has the problem of having a low tumor accumulation rate by itself. An object of the present invention is then to provide a contrast agent for optical imaging having a high tumor accumulation rate.

The present invention provides a compound having at least one organic dye covalently bound to polyethylene glycol, or a salt thereof, wherein the organic dye is a compound represented by the following formula (1), or a salt thereof.

In the formula (1), $R_1$ to $R_8$ may be each independently the same or different, and each independently represent any of a hydrogen atom, an alkyl group having 1 or more and 3 or less carbon atoms, and a sulfonic acid group; $R_9$ to $R_{12}$ may be each independently the same or different, and each independently represent any of a hydrogen atom and an alkyl group having 1 or more and 3 or less carbon atoms; $R_{13}$ and $R_{14}$ may be the same or different, and represent an alkyl group having 1 or more and 5 or less carbon atoms and optionally having a substituent, wherein the substituent is any of a carboxyl group, a sulfonic acid group and a phosphonic acid group; $n_1$ and $n_2$ may be the same or different, and represent 0 or 1; $L_1$ to $L_7$ represent a methine group, wherein the methine group may be each substituted with an alkyl group or may be taken together with the alkyl group to form a 4- to 6-membered ring; and $R_{100}$ represents a phenyl group, a pyridyl group, a benzyl group, or an alkyl group having 1 or more and 5 or less carbon atoms and optionally having a substituent, wherein the substituent is any of an aryl group, an arylalkyl group, a sulfoalkyl group, an alkylthio group, a sulfoalkylthio group, a heterocyclic group, an acylamino group, an arylamino group, an N-aryl-N-alkylamino group, an arylthio group, an aryloxy group, a halogen atom and an acylaminoaryloxy group.

Further features of the present invention will become apparent from the following description of exemplary embodiments.

DESCRIPTION OF THE EMBODIMENTS

Preferred embodiments of the present invention will now be described in detail.

A compound according to an embodiment of the present invention, or a salt thereof is described, but the present invention is not limited thereto. Hereinafter, a case is described where the salt of the compound is a pharmaceutically acceptable salt.

(Contrast Agent for Optical Imaging)

A contrast agent for optical imaging according to the present embodiment includes a plurality of compounds having at least one specific organic dye covalently bound to polyethylene glycol. The contrast agent for optical imaging according to the present embodiment may also include, in addition to the compounds, a dispersion medium, a pharmacologically acceptable additive (for example, vasodilator), albumin, a salt and the like. A capturing molecule described later may also be further bound to the polyethylene glycol in the present embodiment.

Hereinafter, materials forming the contrast agent for optical imaging according to the present embodiment are described in detail.

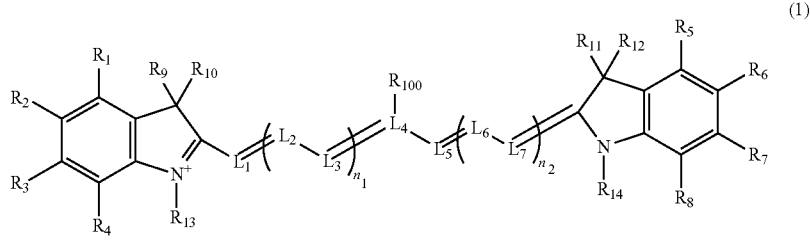

(1)

(Organic Dye)

The organic dye in the present embodiment is a compound represented by the following formula (1), or a pharmaceutically acceptable salt thereof.

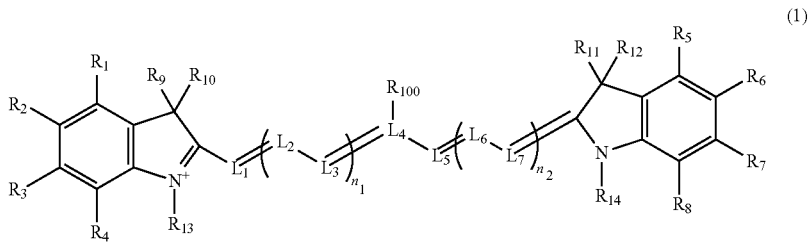

In the formula (1), $R_1$ to $R_8$ may be each independently the same or different, and each independently represent any of a hydrogen atom, an alkyl group having 1 or more and 3 or less carbon atoms, and a sulfonic acid group. $R_1$ to $R_8$ can represent a hydrogen atom or a sulfonic acid group. In the formula (1), $R_9$ to $R_{12}$ may be each independently the same or different, and each independently represent any of a hydrogen atom and an alkyl group having 1 or more and 3 or less carbon atoms. $R_9$ to $R_{12}$ can represent a methyl group.

In the formula (1), $R_{13}$ and $R_{14}$ may be the same or different, and represent an alkyl group having 1 or more and 5 or less carbon atoms and optionally having a substituent. The substituent is any of a carboxyl group, a sulfonic acid group and a phosphonic acid group. $R_{13}$ and $R_{14}$ can be a propyl group having a substituent, and the substituent can be a carboxyl group.

In the formula (1), $n_1$ and $n_2$ may be the same or different, and represent 0 or 1, and $n_1$ and $n_2$ can represent 1.

In the formula (1), $L_1$ to $L_7$ represent a methine group, and the methine group may be each substituted with an alkyl group or may be taken together with the alkyl group to form a 4- to 6-membered ring. In the formula (1), $R_{100}$ represents a phenyl group, a pyridyl group, a benzyl group, or an alkyl group having 1 or more and 5 or less carbon atoms and optionally having a substituent. The substituent is any of an aryl group, an arylalkyl group, a sulfoalkyl group, an alkylthio group, a sulfoalkylthio group, a heterocyclic group, an acylamino group, an arylamino group, an N-aryl-N-alkylamino group, an arylthio group, an aryloxy group, a halogen atom and an acylaminoaryloxy group. $R_{100}$ can represent any of a methyl group, an ethyl group, a phenyl group, a pyridyl group and a benzyl group. The structure represented by the formula (1) has a bulky substituent in the methine chain, and therefore is high in affinity with albumin. When two or more of $R_1$ to $R_8$ represent a sulfonic acid group, dispersibility in an aqueous solution is high.

The organic dye in the present embodiment is represented by, for example, any of the following formulae (2) to (6).

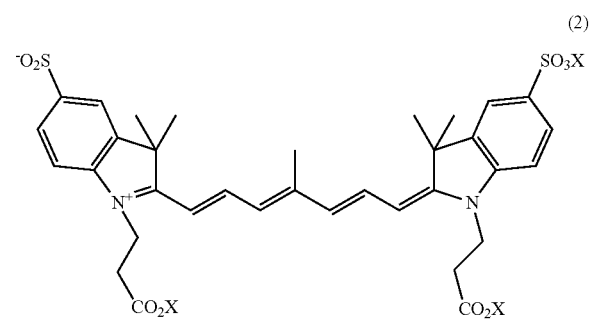

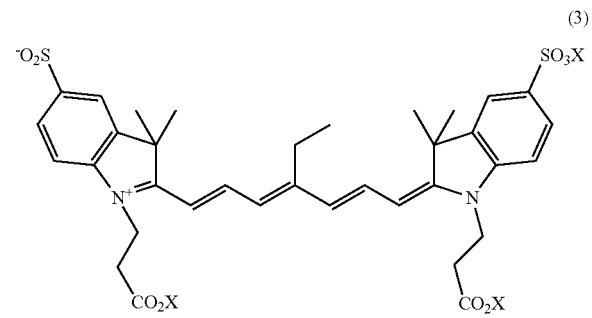

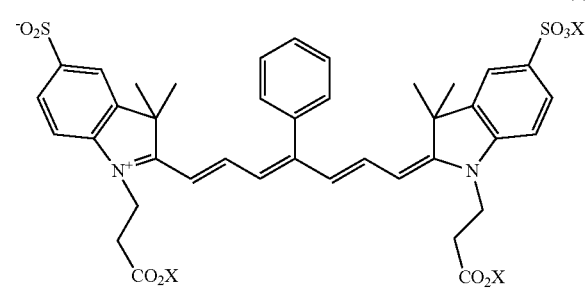

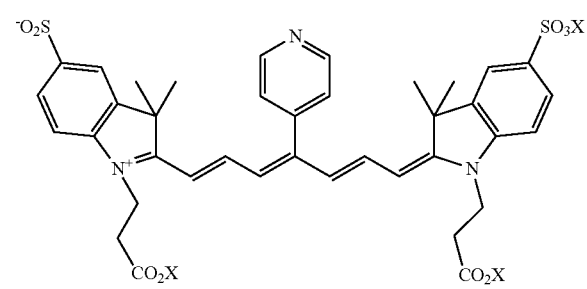

(6)

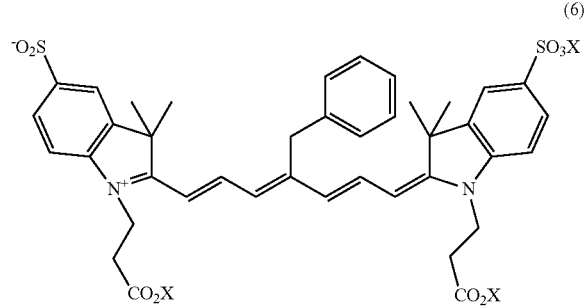

In the formulae (2) to (6), X represents any of a hydrogen atom, a sodium atom and a potassium atom. In the formulae (2) to (6), while one of sulfonic acid groups is represented in an ionized form, various forms can be taken, and, for example, any one of two sulfonic acid groups and two carboxyl groups can be ionized.

The organic dye in the present embodiment can be a compound (hereinafter, sometimes abbreviated as "152C dye") represented by the following formula (7), or a pharmaceutically acceptable salt thereof.

(7)

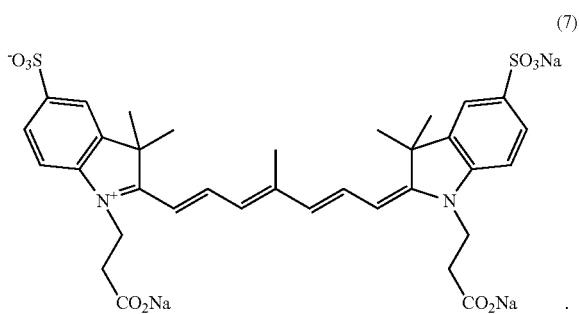

The organic dye in the present embodiment can be an organic dye that absorbs light in a near-infrared wavelength region to emit an acoustic wave. Herein, the light in a near-infrared wavelength region means light at wavelengths of 600 nm to 1300 nm.

(Polyethylene Glycol (PEG))

The compound having polyethylene glycol (PEG) in the present embodiment may include not only a linear compound, but also a branched compound. Hereinafter, polyethylene glycol is sometimes abbreviated as "PEG".

The compound may also have a plurality of amino groups that can be bound to the dye. The reason is that a plurality of dyes can be bound to thereby result in an increase in the number of dyes bound per PEG unit.

Examples of the compound having PEG in the present embodiment include compounds represented by the following formulae (8), (9) and (10).

(8)

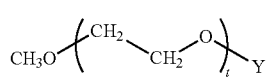

In the formula (8), the dye is introduced via a Y moiety. For example, when Y represents $CH_2CH_2NH_2$, conjugation with a dye having a carboxyl group or a dye having an N-hydroxysuccinimide (NHS) group can be made. When Y represents $CH_2CH_2SH$, conjugation with a dye having a maleimide group or a thiol group can be made. In the formula (8), t preferably denotes an integer of 1 to 2500, further preferably denotes 100 to 1000, particularly preferably denotes 450 or more and 910 or less.

In the formula (8), the molecular weight can be 5000 or more and 40000 or less, and is preferably 10000 or more, particularly preferably 20000 or more.

Examples of the polyethylene glycol represented by the formula (8) include SUNBRIGHT (registered trademark) PA Series (produced by NOF Corporation) (SUNBRIGHT MEPA-20H, SUNBRIGHT MEPA-50H, SUNBRIGHT MEPA-10T, SUNBRIGHT MEPA-12T, SUNBRIGHT MEPA-20T, SUNBRIGHT MEPA-30T, SUNBRIGHT MEPA-40T), SUNBRIGHT (registered trademark) EA Series (produced by NOF Corporation) (SUNBRIGHT ME-020EA, SUNBRIGHT ME-050EA, SUNBRIGHT ME-100EA, SUNBRIGHT ME-200EA, SUNBRIGHT ME-300EA, SUNBRIGHT ME-400EA) and SUNBRIGHT (registered trademark) SH Series (produced by NOF Corporation) (SUNBRIGHT ME-020SH, SUNBRIGHT ME-050SH, SUNBRIGHT ME-100SH, SUNBRIGHT ME-200SH, SUNBRIGHT ME-300SH, SUNBRIGHT ME-400SH).

(9)

In the formula (9), the dye is introduced via a Y moiety. For example, when Y represents $CH_2CH_2CH_2NH_2$, conjugation with a dye having a carboxyl group or a dye having an N-hydroxysuccinimide (NHS) group can be made as in the formula (8).

Examples of the polyethylene glycol represented by the formula (9) include SUNBRIGHT DE-010PA, SUNBRIGHT DE-020PA, SUNBRIGHT DE-034PA, SUNBRIGHT DE-100PA, SUNBRIGHT DE-200PA, SUNBRIGHT DE-300PA, SUNBRIGHT DE-034SH, SUNBRIGHT DE-100SH and SUNBRIGHT DE-200SH produced by NOF Corporation.

(10)

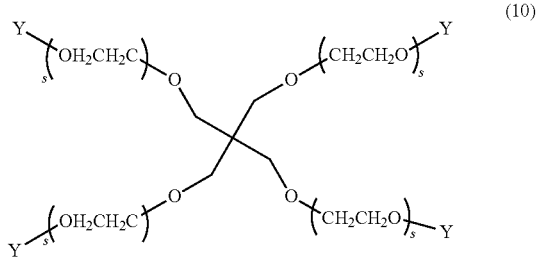

In the formula (10), the dye is introduced via a Y moiety. For example, when Y represents $CH_2CH_2CH_2NH_2$, conjugation with a dye having a carboxyl group or a dye having an N-hydroxysuccinimide (NHS) group can be made as in the formula (8).

The degree s of polymerization of each of four repeating units is mutually independently an integer of 1 to 2500.

The molecular weight can be 1000 to 40000.

In the formula (10), the dye may not be introduced to all four Y(s), and the dyes to be introduced to all Y(s) may be the same or different.

Examples of the polyethylene glycol represented by the formula (10) include SUNBRIGHT PTE-100PA, SUNBRIGHT PTE-150PA, SUNBRIGHT PTE-200PA, SUNBRIGHT PTE-400PA, SUNBRIGHT PTE-050SH, SUN- BRIGHT PTE-100SH and SUNBRIGHT PTE-200SH produced by NOF Corporation.

Other examples can include various PEGs such as SUNBRIGHT GL2-200PA (produced by NOF Corporation), SUNBRIGHT GL2-400PA (produced by NOF Corporation), SUNBRIGHT GL3-400PA 100U (produced by NOF Corporation), SUNBRIGHT HGEO-150PA (produced by NOF Corporation), SUNBRIGHT HGEO-200SH (produced by NOF Corporation), SUNBRIGHT PTE2-200EA (produced by NOF Corporation) and SUNBRIGHT PTE2-400EA (produced by NOF Corporation).

(Composite)

The composite in the present embodiment has at least one organic dye covalently bound to PEG. A composite (which can also be referred to as "compound") having the organic dye represented by any of the formulae (2) to (6) bound to PEG can also be represented as follows.

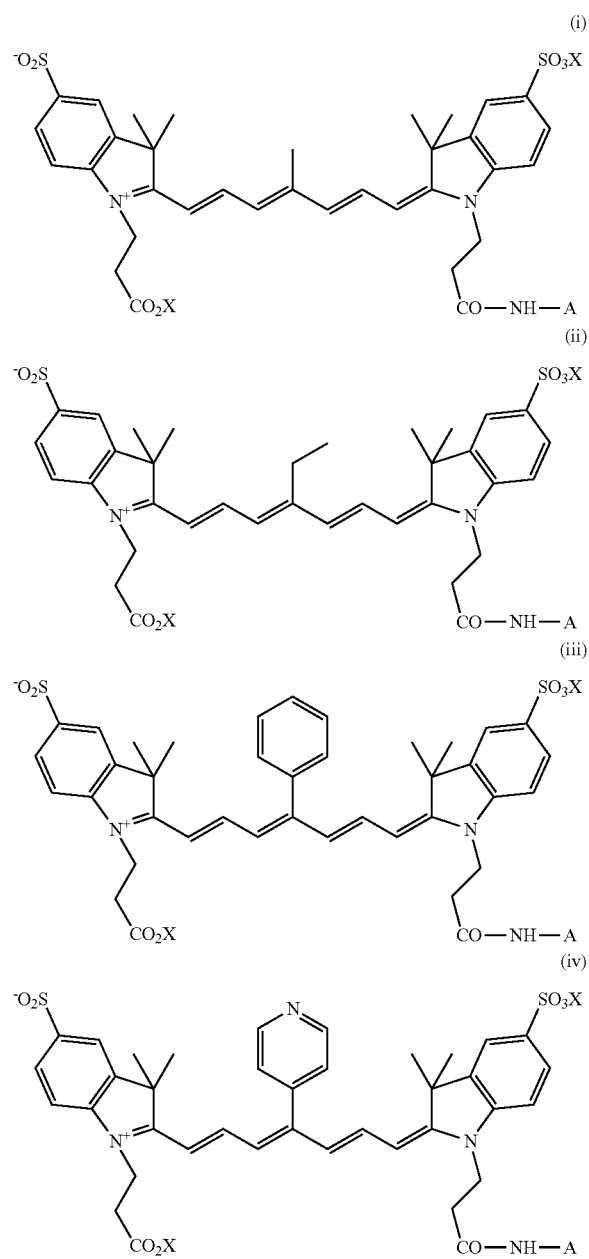

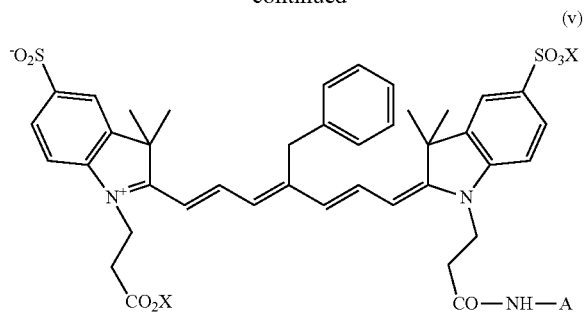

In the formulae (i) to (v), X represents any of a hydrogen atom, a sodium atom and a potassium atom. In the formulae (i) to (v), while one of sulfonic acid groups is represented in an ionized form, another of sulfonic acid groups, or any one of two carboxyl groups may be ionized.

In addition, A can be represented by the following formula (11).

In the formula (11), * represents a bond bound to each N in the formulae (i) to (v). In the formula (11), t denotes an integer of 1 to 2500.

(Dispersion Medium)

Examples of the dispersion medium in the present embodiment include saline, distilled water for injection, phosphate buffered saline (PBS) and an aqueous glucose solution. The contrast agent for optical imaging according to the present embodiment may be dispersed in the dispersion medium in advance, or may be formed into a kit once and dispersed in the dispersion medium and used before administration into a living body.

(Capturing Molecule)

The capturing molecule in the present embodiment is a substance to be specifically bound to a target site such as a tumor, a substance to be specifically bound to a substance present around a target site, or the like, and can be arbitrarily selected from a biological molecule and a chemical substance such as a pharmaceutical product. Specific examples include a protein, an antibody, an antibody fragment, an enzyme, a bioactive peptide, a glycopeptide, a peptide, a sugar chain, a lipid and a molecular recognition compound. Such a substance can be used singly or in combinations of a plurality thereof. A composite in which the capturing molecule is chemically bound can be used to thereby allow specific detection of a target site, and follow-up of dynamics, localization, drug efficacy and metabolism of a target substance to be conducted.

(Method for Preparing Composite)

The method for preparing the composite in the present embodiment includes a step of providing the dye represented by the formula (1) and PEG represented by any of the formulae (8) to (10), and a step of reacting the dye and the PEG derivative. In the reaction step, any method can be utilized such as a method where a condensing agent is used for a reaction of a carboxyl group and an amino group, a method where a salt is formed and condensation is conducted by a dehydration reaction, a method where a dehydrating agent is used, and a method where a carboxyl group is converted to an acid chloride and reacted with an amino group. A carbodiimide-based condensing agent, a phosphoric acid-based condensing agent or the like can be utilized as the condensing agent. Examples of the carbodiimide-based condensing agent can include N,N'-dicyclohexylcarbodiimide (DCC) and water-soluble carbodiimide (WSC).

(Optical imaging method)

The optical imaging method in the present embodiment includes fluorescence imaging where a subject is irradiated with light and the fluorescence is measured, and photoacoustic imaging where a subject is irradiated with light and the acoustic wave (which can also be referred to as "ultrasonic wave") is measured. The contrast agents for the respective procedures can be referred to as "contrast agent for fluorescence imaging" and "contrast agent for photoacoustic imaging", respectively.

(Photoacoustic Imaging Method)

The method for detecting the contrast agent for photoacoustic imaging (PAI) according to the present embodiment, administered into a living body, by use of a photoacoustic imaging apparatus is described. The method for detecting the contrast agent for PAI according to the present embodiment includes the following steps (a) and (b). The photoacoustic imaging method according to the present embodiment, however, may also include any step other than the following:

step (a) of irradiating a subject, to which the contrast agent for PAI according to the present embodiment is administered, with light in the wavelength range from 600 nm to 1300 nm; and step (b) of detecting the acoustic wave emitted from the contrast agent present in the subject.

The method according to the present embodiment may include a step of reconstituting a spatial photoacoustic signal intensity distribution based on the wavelength, the phase, the time information and the like of the acoustic wave obtained in step (b). Three-dimensional image reconstruction can be performed based on the wavelength, the phase and the time information of the acoustic wave obtained in step (b). The data obtained by the image reconstruction may be in any form as long as the positional information on the photoacoustic signal intensity distribution can be figured out. For example, the photoacoustic signal intensity may be expressed in a three-dimensional space or the photoacoustic signal intensity may be expressed on a two-dimensional surface. In addition, the information on the same observation object can be acquired by a different imaging method, and the positional corresponding relationship between such information and the photoacoustic signal intensity distribution can be acquired.

In step (a), a subject to which the contrast agent for PAI according to the present embodiment is administered by a method such as oral administration or injection can be used.

In step (a), an apparatus for irradiation of the subject with light, and an apparatus for detection of the photoacoustic wave emitted from the contrast agent for PAI according to the present embodiment are not particularly limited.

In step (b), a light source for irradiation of the subject with light is not particularly limited as long as the subject can be irradiated with pulsed laser light at one or more wavelengths selected from the range from 600 nm to 1300 nm. Examples of the apparatus for irradiation with pulsed laser light include a titanium-sapphire laser (LT-2211-PC manufactured by Lotis Co., Ltd.), an OPO laser (LT-2214 OPO manufactured by Lotis Co., Ltd.) and an alexandrite laser.

The apparatus for detection of the acoustic wave is not particularly limited, and any of various apparatuses can be used. For example, a commercially available photoacoustic imaging apparatus (Nexus128 manufactured by Endra Inc.) can be used.

The imaging method where the contrast agent for PAI according to the present embodiment is used can allow an intended site such as a tumor, a lymph node or a blood vessel to be imaged through steps (a) and (b).

PAI is a concept including photoacoustic tomography (laminography).

The contrast agent for PAI according to the present embodiment, when administered into a living body, can be more accumulated in a tumor site than a normal site in the living body by use of the enhanced permeability and retention (EPR) effect. As a result, when the contrast agent is administered into a living body and thereafter the acoustic wave emitted from the living body is detected by irradiation of the living body with light, the acoustic wave emitted from a tumor site can be larger than the acoustic wave emitted from a normal site. Accordingly, the contrast agent for PAI according to the present embodiment can be used for imaging a tumor.

The contrast agent for PAI according to the present embodiment can also be used for imaging a lymph node. Furthermore, the contrast agent can be particularly used as a contrast agent for a sentinel lymph node. An organic dye such as ICG, when used as a contrast agent for a sentinel lymph node, has the following problem: the organic dye administered into a body is rapidly transferred into blood and eliminated out of the body, and therefore the observation time is restricted. The contrast agent for PAI according to the present embodiment is larger in molecular size than the organic dye and is decreased in the diffusion speed in a tissue, and as a result, the retention time thereof in a sentinel lymph node is expected to be increased. Accordingly, the contrast agent for PAI according to the present embodiment can be used for imaging a lymph node, in particular, imaging a sentinel lymph node.

EXAMPLES

Hereinafter, the present invention is described in more detail with reference to Examples, but the present invention is not limited to such Examples, and materials, composition conditions, reaction conditions and the like can be freely modified as long as a dye-modified polyethylene glycol having the same function and effect is obtained.

(Calculation of Dye Concentration)

In Examples of the present invention, the dye concentration of dye-modified PEG was calculated from the absorbance at a specific absorption wavelength (765 nm) for the dye used. Specifically, a sample was diluted with 0.9% sodium dodecyl sulfate (SDS) to measure the absorbance, and the dye concentration was calculated from the calibration curve of the dye in SDS, created in advance.

Preparation of 152C-PEG (Composite)

Example A1

Polyethylene glycol (produced by NOF Corporation: SUNBRIGHT ME-050EA, molecular weight: 5000) having an amino group was dissolved in a carbonate buffer (pH 9.6) in a concentration of 5 mg/mL to provide a PEG solution. On the other hand, a compound (152C dye) represented by the formula (7), N-(3-Dimethylaminopropyl)-N'-ethylcarbodiimide hydrochloride (sigma-aldrich) in a molar amount three times the molar amount of the dye, and N-hydroxysuccinimide (Kishida Chemical Co., Ltd.) (hereinafter, sometimes abbreviated as "NHS") in a molar amount 1.5 times the molar amount of the dye were mixed in dimethyl sulfoxide (hereinafter, sometimes abbreviated as "DMSO"), and left to stand at room temperature for 2 hours to provide a solution including 152C dye. Next, the solution including 152C dye was added to the PEG solution so that the mole of 152C dye was five times the mole of the amino group of PEG, and reacted at room temperature for 3 hours. Herein, N-(3-Dimethylaminopropyl)-N'-ethylcarbodiimide hydrochloride above may also be referred to as "water soluble carbodiimide (WSC)".

The liquid medium of the resulting reaction mixed solution was replaced with phosphate buffered saline (PBS) by gel filtration (PD-10 column manufactured by General Electric Company), and undesired substances such as unreacted substances were removed at the same time. The resultant was further allowed to pass through a 0.2-μm filter to prepare contrast agent for photoacoustic imaging (A-1) having a composite (152C-PEG) having 152C dye covalently bound to PEG.

Example A2

Contrast agent for photoacoustic imaging (A-2) having 152C-PEG was prepared by the same method as in Example A1 except that polyethylene glycol (produced by NOF Corporation: SUNBRIGHT ME-100EA, molecular weight: 10000) having an amino group was dissolved in a carbonate buffer (pH 9.6) in a concentration of 10 mg/mL to provide a PEG solution.

Example A3

Contrast agent for photoacoustic imaging (A-3) having 152C-PEG was prepared by the same method as in Example A1 except that polyethylene glycol (produced by NOF Corporation: SUNBRIGHT ME-200EA, molecular weight: 20000) having an amino group was dissolved in a carbonate buffer (pH 9.6) in a concentration of 20 mg/mL to provide a PEG solution.

Example A4

Contrast agent for photoacoustic imaging (A-4) having 152C-PEG was prepared by the same method as in Example A1 except that polyethylene glycol (produced by NOF Corporation: SUNBRIGHT ME-400EA, molecular weight: 40000) having an amino group was dissolved in a carbonate buffer (pH 9.6) in a concentration of 40 mg/mL to provide a PEG solution.

Example A5

Contrast agent for photoacoustic imaging (A-5) having 152C-PEG was prepared by the same method as in Example A1 except that polyethylene glycol (produced by NOF Corporation: SUNBRIGHT DE-200PA, molecular weight: 20000) having an amino group at each of both ends was dissolved in a carbonate buffer (pH 9.6) in a concentration of 10 mg/mL to provide a PEG solution.

Example A6

Contrast agent for photoacoustic imaging (A-6) having 152C-PEG was prepared by the same method as in Example A1 except that four-branched polyethylene glycol (produced by NOF Corporation: SUNBRIGHT PTE-200PA, molecular weight: 20000) having four amino groups in one molecule was dissolved in a carbonate buffer (pH 9.6) in a concentration of 5 mg/mL to provide a PEG solution.

Example A7

Contrast agent for photoacoustic imaging (A-7) having 152C-PEG was prepared by the same method as in Example A1 except that four-branched polyethylene glycol (produced by NOF Corporation: SUNBRIGHT PTE-400PA, molecular weight: 40000) having four amino groups in one molecule was dissolved in a carbonate buffer (pH 9.6) in a concentration of 10 mg/mL to provide a PEG solution.

Comparative Example C1

A compound (152C dye) represented by the formula (7) was dissolved in DMSO and diluted with PBS, and thereafter allowed to pass through a 0.2-μm filter to thereby prepare contrast agent for photoacoustic imaging (C-1) having 152C.

(Evaluation of Unreacted Dye)

The unreacted dye was evaluated as follows. The contrast agent for photoacoustic imaging having 152C-PEG produced was diluted with a SDS sample buffer, applied to Tris-Glycine gel and subjected to SDS-PAGE (polyacrylamide gel electrophoresis) electrophoresis, and thereafter the fluorescence intensity of the band of the unreacted dye was measured using ODYSSEY (registered trademark) CLx Infrared Imaging System (manufactured by LI-COR Inc.) to thereby evaluate the rate of the unreacted dye incorporated. It was thus confirmed that the rate of the unreacted dye incorporated was as low as 3.7 to 6.9% with respect to 152C-PEG.

(Quantitative Determination of Tumor Accumulation Properties and Blood Level)

In order to confirm tumor accumulation properties of the contrast agent for photoacoustic imaging prepared in each of Examples and Comparative Example, the contrast agent was administered to a tail vein of a tumor-bearing mouse having colon 26 cell lines transplanted. The amount of administration was 13 nmol in terms of the amount of dye. At 24 hours after the administration, blood was taken from the tail of the mouse, the mouse was euthanized, and thereafter a colon 26 tumor tissue was harvested. The tumor tissue was transferred to a plastic tube, an aqueous 1% Triton X-100 solution was added thereto in an amount 1.25 times the weight of the tumor tissue, and the resultant was homogenized by use of a plastic pestle. Next, the homogenate solution was subjected to a centrifugation operation (16000×G at 4° C. for 5 minutes) and the supernatant thereof was recovered, and dimethyl sulfoxide (DMSO) (18 μL) was added to the supernatant (2 μL). An aqueous 1% Triton X-100 solution (9 μL) and DMSO (9 μL) were added to the blood (2 μL) taken. The fluorescence intensities of the homogenate solution and the blood were measured on a 48-well plate by use of ODYSSEY (registered trademark) CLx Infrared Imaging System (manufactured by LI-COR Inc.), to thereby quantitatively determine the amount of the compound according to each of the present Example and Comparative Example in each of the tumor tissue and the blood. The ratio (% injected dose: abbreviated as "% ID") of the dye transferred to the tumor tissue relative to the amount of administration (dye: 13 nmol), per unit weight of the tumor tissue, was designated as the tumor accumulation rate (% ID/g) of the compound.

Herein, the amount of accumulation of the compound in the tumor tissue, thus determined, was defined as an index of "T (% ID/g)", the retention rate of the dye of the compound in the blood was defined as an index of "B (% ID/g)", and the value obtained by dividing the value of T by the value of B was defined as an index of T/B (tumor accumulation rate/retention rate in blood).

The calculation results of the tumor accumulation rate, the retention rate in blood and the T/B (tumor accumulation rate/retention rate in blood) of each contrast agent are shown in Table 1. In Table 1, "N.D." represents the data that is equal to or lower than the detection limit. It was confirmed that 152C dye and PEG were conjugated to result in an enhancement in tumor accumulation rate. Additionally, a composite of 152 dye and PEG, exhibiting a T/B of 2 or more, a high tumor/blood ratio, was obtained. In particular, contrast agent (A-3) exhibited a T/B of 22, a high tumor/blood ratio.

TABLE 1

|  | Contrast agent (A-1) | Contrast agent (A-2) | Contrast agent (A-3) | Contrast agent (A-4) | Contrast agent (A-5) | Contrast agent (A-6) | Contrast agent (A-7) | Contrast agent (C-1) |
|---|---|---|---|---|---|---|---|---|
| Molecular weight of polyethylene glycol | 5000 | 10000 | 20000 | 40000 | 20000 | 20000 | 40000 | — |
| Tumor accumulation rate (% ID/g) | 0.37 | 0.50 | 3.9 | 14 | 7.6 | 10 | 12 | N.D. |
| Retention rate in blood (% ID/g) | N.D. | N.D. | 0.18 | 6.2 | 3.2 | 3.9 | 9.2 | N.D. |
| T/B (Tumor accumulation rate/Retention rate in blood) | — | — | 22 | 2.3 | 2.4 | 2.6 | 1.2 | — |

The present invention can allow polyethylene glycol to be covalently bound to the dye represented by the formula (1), resulting in an increase in tumor accumulation properties. Additionally, a high tumor/blood ratio can be exhibited and a tumor can be selectively detected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-021967, filed Feb. 8, 2016, which is hereby incorporated by reference herein in its entirety.

What is claimed is:

1. A compound consisting of at least one organic dye covalently bound to a polyethylene glycol, or a salt thereof, wherein the organic dye is represented by any of formulae (2) to (6), and wherein the polyethylene glycol is represented by any of formulae (8) to (10):

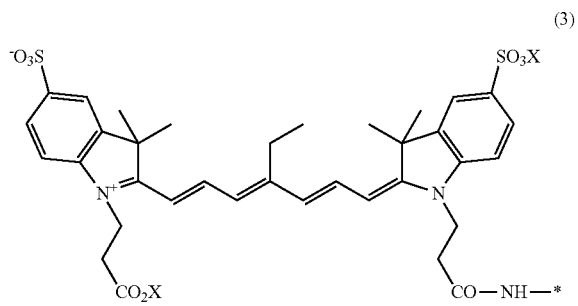

(2)

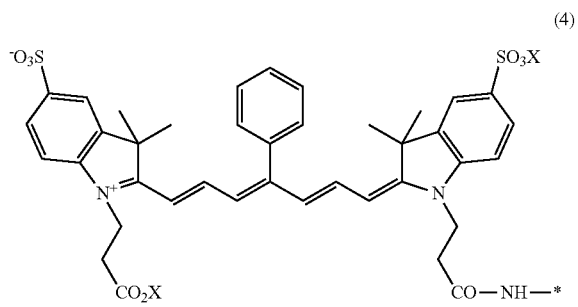

(3)

(4)

(5)

-continued (6)

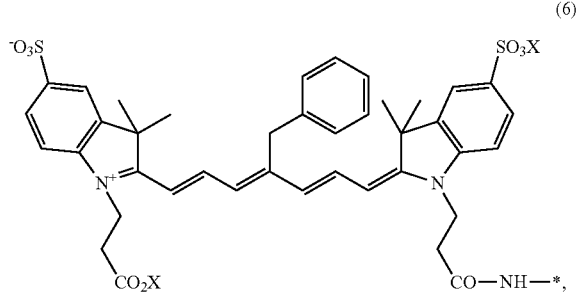

wherein, in the formulae (2) to (6):
X represents any of a hydrogen atom, a sodium atom, and a potassium atom; and
\* represents a bond to O adjacent to Y in the formulae (8) to (10), either directly or through a linker;

(8)

$$CH_3O\text{-}(CH_2\text{-}CH_2\text{-}O)_t\text{-}Y,$$

wherein, in the formula (8):
Y represents a bond to N adjacent to \* in the formulae (2) to (6), either directly or through a linker; and
t is an integer of 1 or more;

$$Y\text{-}(OCH_2CH_2)_n\text{-}O\text{-}Y, \quad (9)$$

wherein, in the formula (9):
Y represents a bond to \* in the formulae (2) to (6), either directly or through a linker, and the organic dye at each Y may be the same or different; and
n is an integer of 1 or more;

(10)

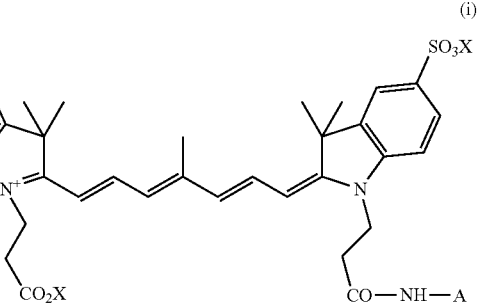

wherein, in the formula (10):
Y represents a bond to \* in the formulae (2) to (6), either directly or through a linker, and the organic dye at each Y may be the same or different; and
s is an integer of 1 or more.

2. The compound or salt thereof according to claim 1, wherein a molecular weight of the polyethylene glycol is 20000 or more.

3. The compound or salt thereof according to claim 1, which has a molecular weight of 1000 to 40000.

4. The compound or salt thereof according to claim 1, wherein the linker is $CH_2CH_2$ or $CH_2CH_2CH_2$.

5. The compound or salt thereof according to claim 1, wherein, in the formulae (8) to (10), each of t, n, and s is, independently, an integer of 1 to 2500.

6. The compound or salt thereof according to claim 1, wherein, in the formula (8), t is an integer of 100 to 1000.

7. The compound or salt thereof according to claim 1, wherein, in the formula (8), t is an integer of 450 to 910.

8. The compound or salt thereof according to claim 1, wherein a capturing molecule is bound to the polyethylene glycol.

9. A compound represented by any of formulae (i) to (v), or a salt thereof:

(i)

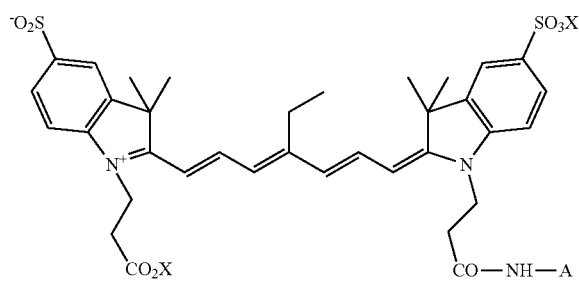

(ii)

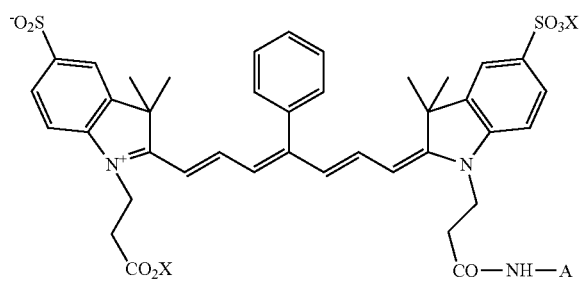

(iii)

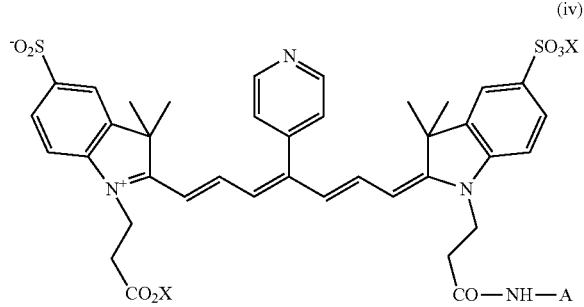

(iv)

-continued

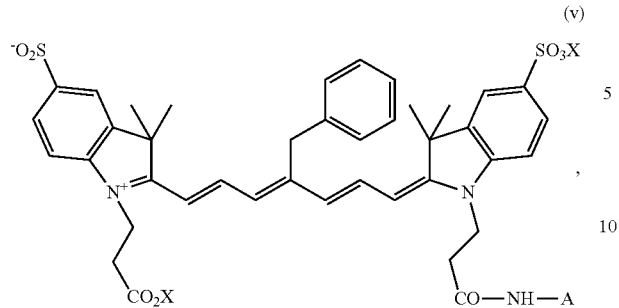

(v)

wherein, in the formulae (i) to (v), X represents any of a hydrogen atom, a sodium atom, and a potassium atom, and A represents a polyethylene glycol structure.

10. The compound or salt thereof according to claim 9, wherein A is represented by formula (11):

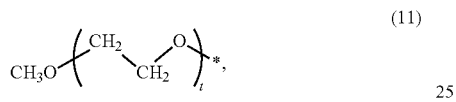

(11)

wherein, in the formula (11), * represents a bond to N in each of the formulae (i) to (v), and t is an integer of 1 to 2500.

11. A contrast agent for optical imaging, comprising:
the compound or salt thereof according to claim 1; and
a dispersion medium.

* * * * *